United States Patent
Gottmann et al.

(10) Patent No.: US 9,513,243 B2
(45) Date of Patent: Dec. 6, 2016

(54) CRACK DETECTION IN CERAMICS USING ELECTRICAL CONDUCTORS

(71) Applicant: BLOOM ENERGY CORPORATION, Sunnyvale, CA (US)

(72) Inventors: Matthias Gottmann, Sunnyvale, CA (US); Sanjiv Kapoor, Sunnyvale, CA (US)

(73) Assignee: BLOOM ENERGY CORPORATION, Sunnyvale, CA (US)

( * ) Notice: Subject to any disclaimer, the term of this patent is extended or adjusted under 35 U.S.C. 154(b) by 0 days.

(21) Appl. No.: 14/873,686

(22) Filed: Oct. 2, 2015

(65) Prior Publication Data

US 2016/0077033 A1    Mar. 17, 2016

Related U.S. Application Data (63) Continuation of application No. 13/531,631, filed on Jun. 25, 2012, now Pat. No. 9,176,085.

(60) Provisional application No. 61/535,121, filed on Sep. 15, 2011.

(51) Int. Cl.
    G01N 27/20    (2006.01)
    G01N 27/82    (2006.01)
    H01M 8/12     (2016.01)

(52) U.S. Cl.
    CPC .............. *G01N 27/20* (2013.01); *H01M 8/124* (2013.01); *Y02E 60/521* (2013.01); *Y02E 60/525* (2013.01); *Y02P 70/56* (2015.11)

(58) Field of Classification Search
    CPC . G01N 27/20; G01N 2291/0289; G01N 25/72
    USPC ........ 324/718, 439; 429/426, 439, 482, 483, 429/535
    See application file for complete search history.

(56) References Cited

U.S. PATENT DOCUMENTS

| | | | |
|---|---|---|---|
| 7,098,163 B2 | 8/2006 | Hampden-Smith et al. | |
| 7,404,750 B2 | 7/2008 | Dean et al. | |
| 7,670,700 B2 | 3/2010 | Imamura et al. | |
| 8,358,137 B2 * | 1/2013 | Uchiyama ......... | H01M 8/04104 324/464 |
| 2003/0175569 A1 | 9/2003 | Inagaki et al. | |
| 2004/0001994 A1 | 1/2004 | Marina et al. | |
| 2004/0095127 A1 | 5/2004 | Mohri et al. | |
| 2007/0184331 A1 | 8/2007 | Kim et al. | |
| 2007/0231676 A1 | 10/2007 | Cassidy et al. | |
| 2008/0096080 A1 | 4/2008 | Batawi et al. | |
| 2009/0029195 A1 | 1/2009 | Gauckler et al. | |
| 2009/0108856 A1 | 4/2009 | Yonushonis et al. | |
| 2010/0003568 A1 | 1/2010 | Sugawara et al. | |
| 2010/0206455 A1 | 8/2010 | Uchiyama | |
| 2013/0069663 A1 | 3/2013 | Gottmann et al. | |

\* cited by examiner

*Primary Examiner* — Tung X Nguyen
*Assistant Examiner* — Neel Shah
(74) *Attorney, Agent, or Firm* — The Marbury Law Group PLLC (57) ABSTRACT

Various embodiments provide methods and systems for detecting cracks in ceramic electrolytes using electrical conductors. A method for testing an electrolyte material, such as a ceramic electrolyte material for use in a solid oxide fuel cell device, includes providing a conductive path on the electrolyte material, electrically connecting a probe across the conductive path, and measuring a value associated with the conductive path to determine the presence or absence of a crack in the material.

20 Claims, 5 Drawing Sheets

CRACK DETECTION IN CERAMICS USING ELECTRICAL CONDUCTORS

BACKGROUND

Solid oxide fuel cells ("SOFC's") are solid-state devices which use an oxygen ion conducting ceramic electrolyte to produce electrical current by transferring oxygen ions from an oxidizing gas stream at the cathode of the fuel cell to a reducing gas stream at the anode of the fuel cell. The oxidizing flow is typically air, while the fuel flow can be a hydrocarbon fuel, such as methane, natural gas, pentane, ethanol, or methanol. The fuel cell, operating at a typical temperature between 750° C. and 950° C., enables the transport of negatively charged oxygen ions from the cathode flow stream to the anode flow stream, where the ion combines with either free hydrogen or hydrogen in a hydrocarbon molecule to form water vapor and/or with carbon monoxide to form carbon dioxide. The excess electrons from the negatively charged ion are routed back to the cathode side of the fuel cell through an electrical circuit completed between anode and cathode, resulting in an electrical current flow through the circuit. This type of fuel cell is seen as especially promising in the area of distributed stationary power generation.

Fuel cell stacks are frequently built from a multiplicity of cells in the form of planar elements, tubes, or other geometries. Fuel cell stacks, particularly those with planar geometry, often use seals between electrolyte and interconnect surfaces to contain fuel and air at various locations within the stack. The stacks are often internally manifolded for fuel and/or air flow, and the ceramic electrolyte material can include internal openings or holes to accommodate fluid flow within the stack.

Cracks in the ceramic electrolyte used in solid oxide fuel cells are a primary cause of failure of these devices. The fuel riser openings, which may be circular holes, cause stress concentrations in the ceramic electrolyte and many cracks are found in the vicinity of these openings. Currently, fuel cell stacks undergo an elaborate inspection process including electrical measurements as well as visual inspections to detect cracks as early as possible in the manufacturing process and to eliminate defective cells.

The current inspection processes for detecting cracks in the electrolyte are time-consuming and labor-intensive and often fail to adequately detect cracks. An undetected crack can result in catastrophic failure of the fuel cell stack. There is therefore a need for improvements in the detection of cracks in ceramic electrolyte material.

SUMMARY

Embodiments include methods for testing an electrolyte material, which comprise providing an electrolyte material having a conductive path, electrically connecting a probe across the conductive path, and measuring a value associated with the conductive path to determine the presence or absence of a crack in the electrolyte material.

Further embodiments include an apparatus for testing an electrolyte material which comprises a support for holding an electrolyte material having a conductive path provided on the material, a probe for making an electrical connection across the conductive path, and a measurement device coupled to the probe that measures an electrical characteristic of the conductive path to detect the presence or absence of a crack in the electrolyte material Further embodiments include a fuel cell which comprises an electrolyte, an anode, a cathode, and a conductive path on the electrolyte and electrically isolated from the anode and the cathode.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The various embodiments provide systems and methods for testing material properties. Further embodiments employ these systems and methods in the improved detection of cracks in an electrolyte, and in particular a ceramic electrolyte, used in fuel cell systems. Improved detection of cracks can help reduce catastrophic stack failure and can lower costs and improve reliability of fuel cell systems.

Embodiments include methods for testing an electrolyte material, such as a ceramic electrolyte material for use in a solid oxide fuel cell device, which comprise providing an electrolyte material having a conductive path, electrically connecting a probe across the conductive path, and measuring a value associated with the conductive path to determine the presence or absence of a crack in the material.

In embodiments, the probe can be an ohmmeter, and measures a resistance across the conductive path. The measured resistance can be compared to an expected resistance and a difference between the measured and expected resistance can indicate the presence of a crack in the material. For example, a measurement of a very high or infinite resistance can indicate a discontinuity in the conductive path and a crack in the underlying electrolyte material.

Other characteristics of the conductive path, such as current, voltage and/or power, can be measured to detect cracks. In one embodiment, a current is generated in the conductive path, and is increased until the conductive path burns out. The burnout characteristics of the path, such as the current required to achieve burnout, can be measured to detect the presence or absence of cracks, if the burnout current varies from an expected or baseline value of the current.

The conductive path can be a patterned trace formed using thin-film or thick-film processing techniques. The trace can be narrow (e.g., less than about 10 microns wide) and thin (e.g., less than about 1 micron in height or thickness), and can be made from suitable conductive materials, such as noble metals (e.g., platinum, gold, silver), conductive oxides, or various combinations of materials.

In preferred embodiments, one or more conductive paths are provided on an electrolyte material, and can be located on crack-prone regions of the electrolyte, such as proximate openings or holes within the electrolyte (e.g., riser channels), or near the corners and edges of the electrolyte. The present method can be used to detect the presence of cracks over a wide range of temperatures, including from below room temperature to at or above fuel cell operating temperatures. The method can be used to detect cracks in the electrolyte of an operating fuel cell device.

In further embodiments, a testing apparatus utilizes the present testing process to detect cracks in an electrolyte material. In other embodiments, a fuel cell includes an electrolyte having a conductive path for detection of cracks in the electrolyte.

In one aspect, the present invention provides a highly-reliable and easily-implemented technique for detecting cracks in a ceramic electrolyte material, which is expected to greatly improve the fabrication process for solid oxide fuel cell devices. It is anticipated that the present detection technique will result in lower costs for these devices, since defective stacks can be more easily identified and removed at an earlier stage of production and/or use. Furthermore, the present crack detection methodology should help lower production costs of many fuel cell systems, since the current labor-intensive and time-consuming crack detection processes can now be avoided.

Figure 1:
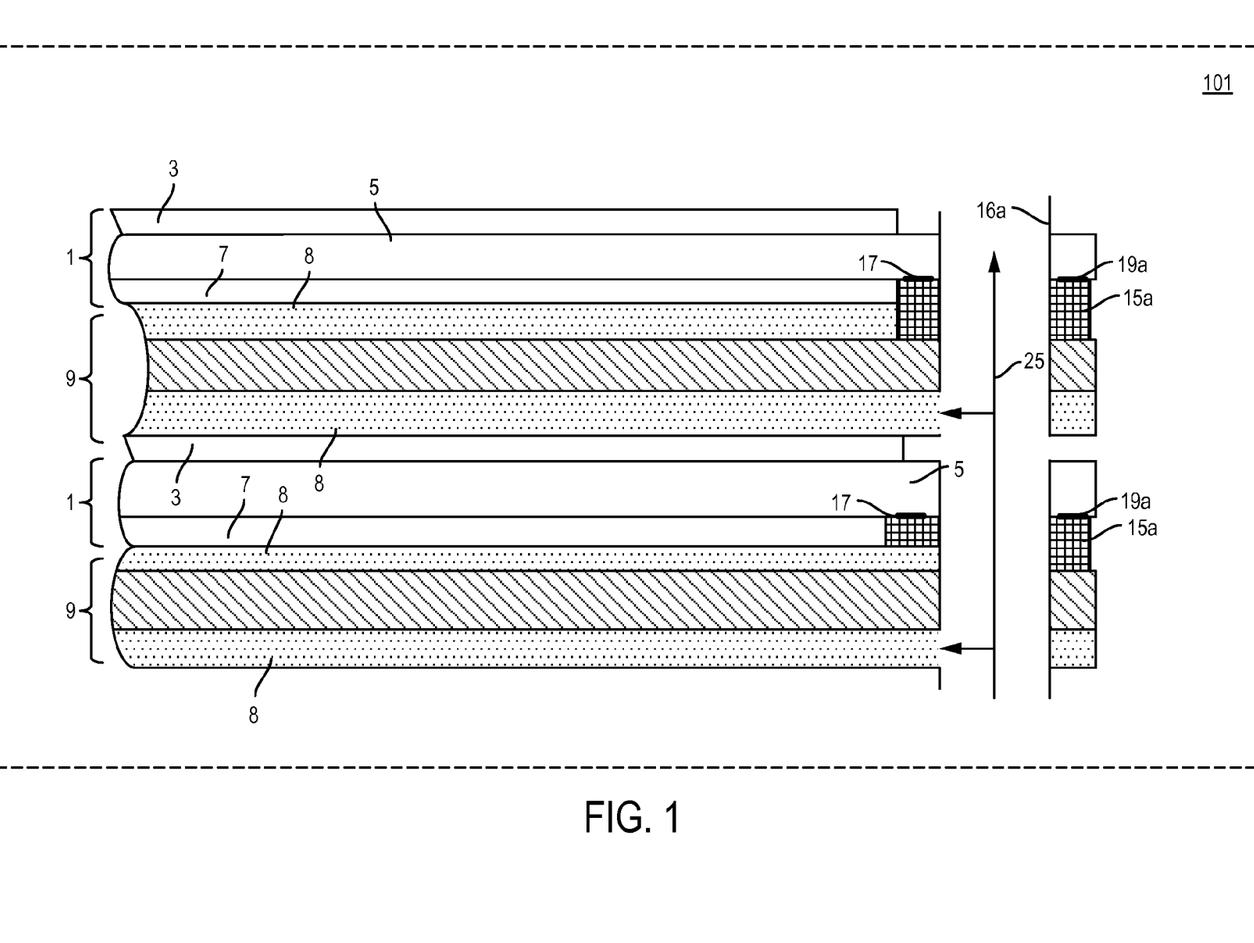
FIG. 1 illustrates a side cross-sectional view of a SOFC stack.

FIG. 1 illustrates a SOFC stack in which each SOFC 1 comprises a cathode electrode 7, a solid oxide electrolyte 5, and an anode electrode 3. Fuel cell stacks are frequently built from a multiplicity of SOFC's 1 in the form of planar elements, tubes, or other geometries. Fuel and air has to be provided to the electrochemically active surface, which can be large.

Figure 2A:
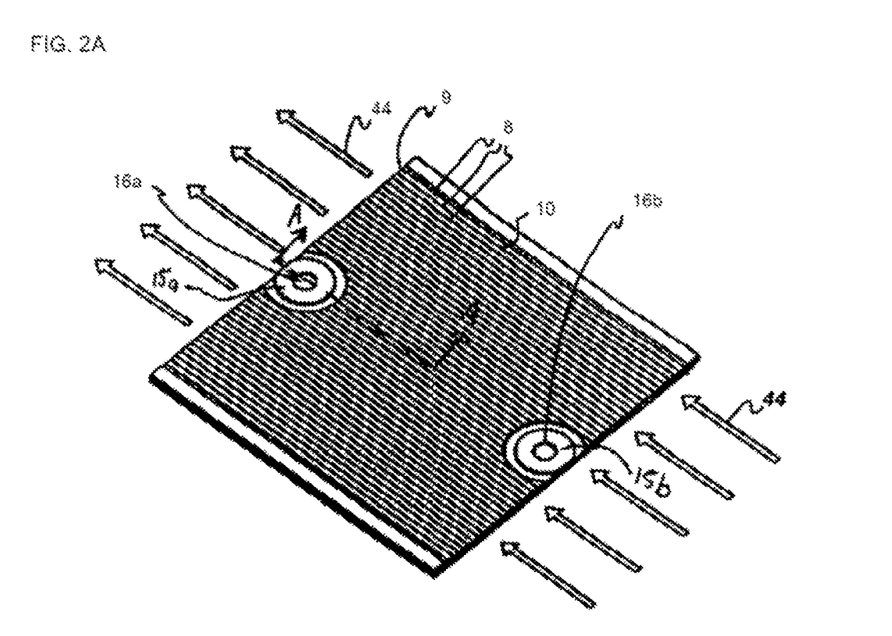
FIG. 2A is a perspective view of a cathode flow side of an interconnect for use in the SOFC stack of FIG. 1.
Figure 2B:
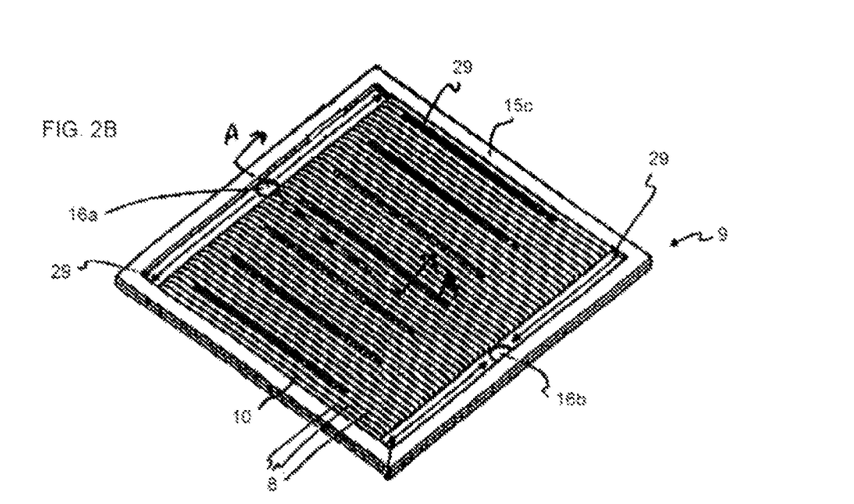
FIG. 2B is a perspective view of the anode flow side of the interconnect.

The gas flow separator 9 (referred to as a gas flow separator plate when part of a planar stack) separates the individual cells in the stack. As illustrated in FIGS. 2A and 2B, which show, respectively, top and bottom views of a gas flow separator 9, the separator 9 contains gas flow passages or channels 8 between ribs 10. The gas flow separator plate separates fuel, such as a hydrocarbon fuel, flowing to the fuel electrode (i.e. anode 3) of one cell in the stack from oxidant, such as air, flowing to the air electrode (i.e. cathode 7) of an adjacent cell in the stack. Frequently, the gas flow separator plate 9 is also used as an interconnect which electrically connects the anode or fuel electrode 3 of one cell to the cathode or air electrode 7 of the adjacent cell. In this case, the gas flow separator plate which functions as an interconnect is made of or contains electrically conductive material. FIG. 1 shows that the lower SOFC 1 is located between two interconnects 9. The portions of interconnects 9 shown in side cross-section in FIG. 1 are provided along lines A-A in FIGS. 2A and 2B.

The SOFC stack in this embodiment includes at least one riser channel 16a for providing fuel to the anode-side of the SOFC 1, as illustrated by arrow 29. The riser channel 16a generally comprises a fuel inlet riser opening or hole that extends through at least one layer of the fuel cells. For example, in the embodiment of FIG. 1, the riser channel 16a extends through multiple electrolyte layers 5 of the stack, and interconnects 9 between each of the electrolytes 5. As illustrated in FIGS. 1 and 2B, the fuel flows through the inlet riser channel 16a to the anode-side of each fuel cell. There, the fuel flows over the fuel cell anode 3 via gas flow channels 8 formed in the gas flow separator/interconnect plate 9, and then exits through separate outlet riser channel 16b.

Seals 15a, 15b seal the respective risers 16a, 16b on the cathode-sides of the interconnect and fuel cell to prevent fuel from reaching the cathode electrode of the fuel cell. The seals may have a donut or hollow cylinder shape as shown so that the risers 16a, 16b extend through the hollow middle part of the respective seals 15a, 15b. A peripheral seal 15c seals the anode-sides of the interconnect and fuel cell to prevent air from reaching the anode electrode of the fuel cell.

The SOFC 1 in this embodiment is configured for a stack that is internally manifolded for fuel and externally manifolded for air. Thus, the stack is open on the air inlet and outlet sides, as indicated by the air-flow arrows 44 in FIG. 2A. Alternatively, the SOFC 1 may be configured for a stack which is internally manifolded for both air and fuel. In this case, the electrolyte would contain additional air inlet and outlet openings.

Figure 3:
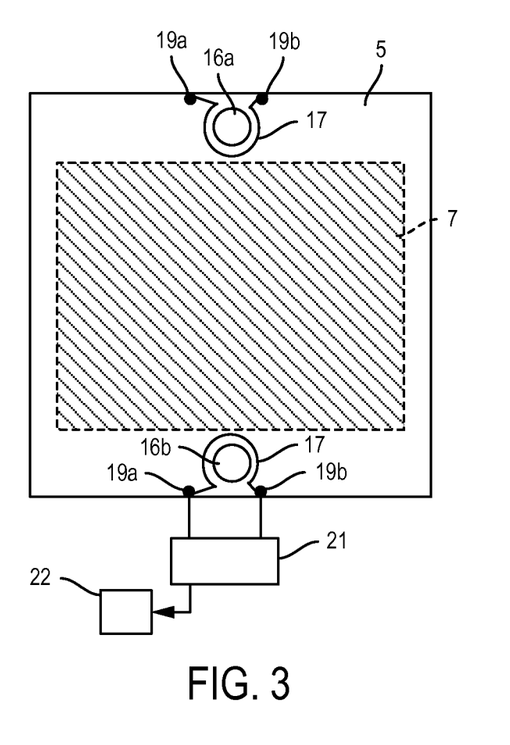
FIG. 3 is a plan view of a fuel cell electrolyte with conductive traces for crack detection.

FIG. 3 is a plan view of a solid oxide electrolyte 5. The electrolyte 5 may comprise a stabilized zirconia, such as scandia stabilized zirconia (SSZ) or yttria stabilized zirconia (YSZ). Alternatively, the electrolyte 5 may comprise another ionically conductive material, such as a doped ceria. In this embodiment, the electrolyte 5 has a planar geometry, although it will be understood that other geometries, such as a tubular geometry, could be utilized. Riser channels 16a, 16b, which in this embodiment comprise circular holes, extend through the electrolyte 5. A cathode (e.g., air) electrode 7 is shown covering part of the surface of the electrolyte 5.

The ceramic electrolyte material should generally be free of defects, including cracks. Small cracks in the electrolyte material can lead to cell cracking and catastrophic failure of the fuel cell stack during high-temperature operation. The embodiment methods and systems provide ways to detect cracks in ceramic electrolytes using electrical conductors. The present detection methods and systems can be utilized at elevated temperature, including the operating or test temperature of the fuel cell (e.g., after the stack is placed in a hot box and operated to generate electricity and/or tested at high temperature before operation), as well as at lower temperatures, such as room temperature (e.g., in a test station before the stack is placed into a hot box for operation).

A first embodiment, as shown in FIGS. 1 and 3, includes one or more small conductive paths 17 that are provided on or within the ceramic electrolyte 5. The conductive path 17 can be used to detect cracks that cross the path. In preferred embodiments, one or more paths 17 are designed and located to detect virtually all cracks that occur in the vicinity of the riser channels 16a, 16b.

In one embodiment, a conductive path 17 is provided on a surface of the electrolyte 5. As shown in FIG. 3, the conductive path 17 is provided on the cathode (e.g., air) side surface of the electrolyte 5. However, the path 17 may also be located on the anode (e.g., fuel) surface of the electrolyte. The conductive path 17 on the electrolyte 5 may be electrically isolated from an electrode (e.g., anode 3 and/or cathode 7) on the electrolyte 5 by locating the path 17 on the electrolyte 5 such that it does not physically contact the electrodes 3 and 7. The conductive path 17 can be formed by patterning a trace of a conductive material on the electrolyte 5. In other embodiments, a conductive element, such as a thin wire, can be provided on the electrolyte 5. In preferred embodiments, the path 17 has a narrow width, generally less than about 10 microns, and can be between about 5 and 10 microns wide. The path 17 can also be very thin in height, and in some embodiments can extend less than about 1 micron, such as 0.1-0.75 microns, above the surface of the electrolyte 5. Where the path 17 is proximate to an opening in the electrolyte 5, such as the riser channels 16a, 16b shown in FIG. 3, the path 17 preferably surrounds at least 50% of the diameter of the opening. The conductive path 17 can be formed and/or patterned using any suitable process, such as thin film and/or thick film processing techniques. Such techniques include physical vapor deposition (e.g., sputtering), plating, screen printing, etc.

In some embodiments, the conductive path 17 can comprise one or more noble metals, such as platinum, gold and silver. These metals are advantageous because they can be readily applied and only small amounts are needed to form the path. In addition, these materials generally do not interact with adjacent components. Conductive oxides such as perovskite materials (e.g., LSM, LSCr, LSCo, etc.) can also be used, but their room temperature conductivity is lower, and material compatibility needs to be carefully considered. However, the conductive oxide may comprise the same material as an electrode, such as cathode electrode 7, and may be formed and patterned during the same step as the electrode.

The conductive path 17 can terminate in one or more contact areas 19a, 19b. The contact areas 19a, 19b can be made larger (e.g., wider and thicker) than the path 17. Areas 19a, 19b are preferably located near the edge of the electrolyte for easy access. In one embodiment, an electrical probe 21, such as an ohmmeter, can be placed across the contact areas 19a, 19b to measure a value associated with the conductive path 17. For example, where the probe 21 is an ohmmeter, the resistance of the path 17 is measured. Without wishing to be bound by any particular theory of operation, it is believed that if the conductive path 17 crosses a crack in the electrolyte 5, the conductive path 17 is disrupted and an infinite resistance will be measured.

In general, given the known geometry of the conductive path and the resistivity and/or conductivity of the material used, an expected value for the electrical resistance of the path 17 can be estimated or determined. For example, the resistance, R, of the path 17 can be calculated or estimated using the well-known equation $R=\rho \cdot (1/A)$, where 1 is the length of the conductor in meters (m), A is the cross-section area of the conductor in square meters ($m^2$), and $\rho$ is the electrical resistivity of the material in ohm-meters ($\Omega \cdot m$). For high-temperature measurements, the temperature-dependence of the material resistivity can also be factored into the calculation or estimation. Where the value measured by the probe 21 deviates from this expected value by a predetermined amount, such as where the measured resistance is much larger than the expected value, this can indicate the presence of a crack in the electrolyte.

Figure 4:
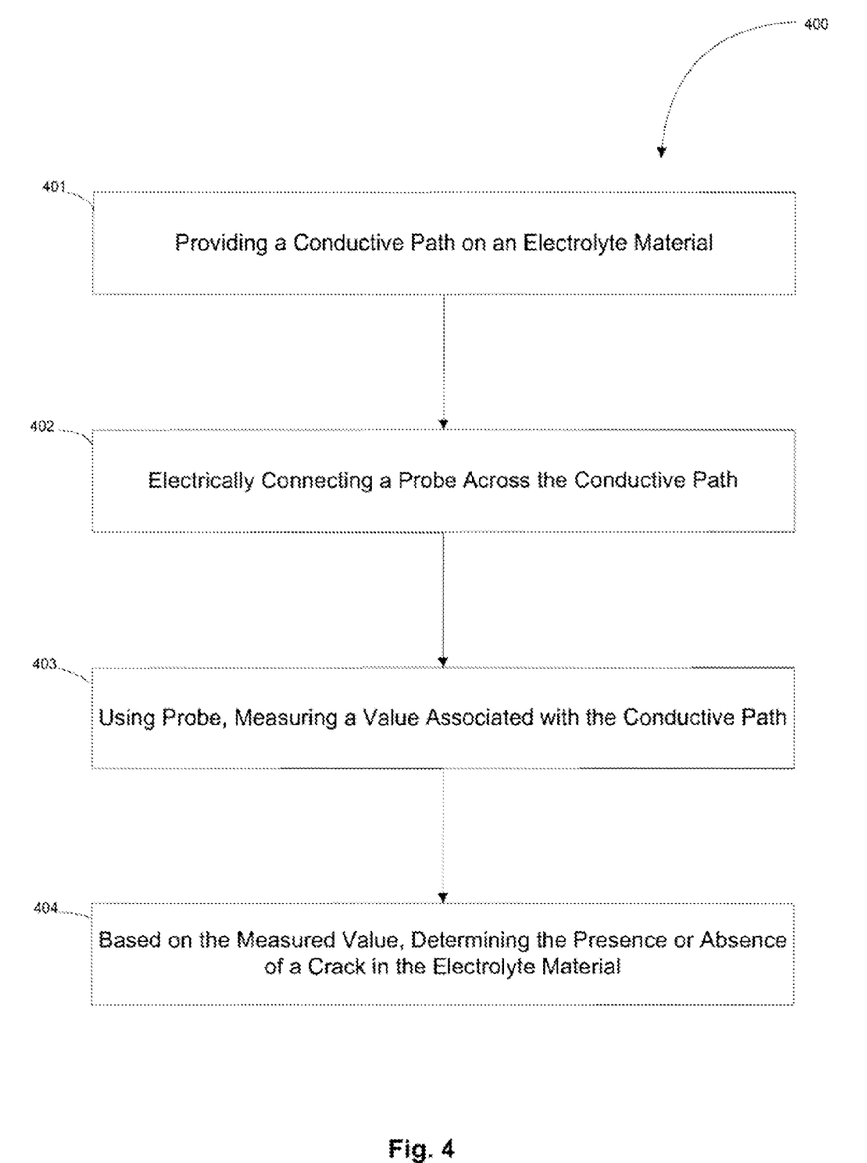
FIG. 4 is a flow chart illustrating an embodiment method for detecting cracks in a fuel cell electrolyte using electrically conductive paths.

FIG. 4 illustrates an embodiment method 400. In step 401, a conductive path is provided on an electrolyte material. As discussed above, the path can be a patterned conductive trace formed, for example, using thin-film or thick-film processing techniques. In certain embodiments, the step of providing the conductive path on the electrolyte can be an automated process, and can be performed, for example, as part of the fabrication process of the cell. In general, the conductive path is provided on a crack-prone area of the cell, such as proximate to a riser channel or near the corners or edges of the electrolyte. In some embodiments, multiple conductive paths can be provided on a single electrolyte, and conductive paths can be provided on or extending between multiple surfaces of the electrolyte (e.g., top, bottom and side surfaces), as well as on internal surfaces, such as within a riser channel.

In step 402, a probe is electrically connected across the conductive path, and a value associated with the path is measured at 403. In some embodiments, the conductive path terminates in a pair of contact areas, and the probe contacts against the contact areas to obtain a measurement. In other embodiments, the conductive path can terminate in a pair of lead wires that extend away from the electrolyte, and the probe can connect to the lead wires. As discussed above, the probe can be an ohmmeter and the value associated with the path that is measured is the resistance value of the path. In other embodiments, the probe could measure other values of the conductive path, such as voltage, current, power, etc.

In step 404, the presence of absence of a crack is determined based on the measured value associated with the path. As discussed above, the presence of a crack can be determined when the measured value deviates from a baseline or expected value by a pre-determined amount. The baseline value can be stored in a memory (e.g., a look-up table), and a comparison between the baseline value and the measured value can be done by a measurement device 22, which may be a logic device (e.g., computer). For example, where the measured value is the resistance of the conductive path, a large or infinite resistance can indicate a disruption in the electrical path and the presence of a crack in the electrolyte.

In an alternate embodiment, the measured value associated with the path can be the current in the path, and the presence or absence of a crack is determined based on the burnout characteristics of the conductive path. In this method, a current is generated in the trace by device 21, and the current is increased until the trace burns out. Based on the burnout characteristics (i.e., the current required to burn out the trace and/or the time required to burn out the trace for a given current), even small distortions in the trace can be detected. This technique can be used to detect insipient cracks in the electrolyte by comparing the current and/or time required to burn out the trace to an expected or baseline value.

Figure 5:
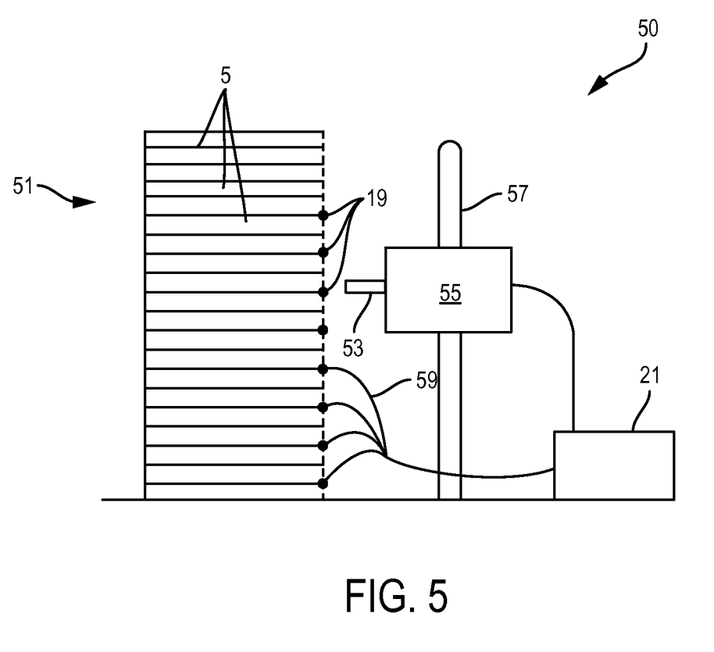
FIG. 5 schematically illustrates an apparatus for detecting cracks in a fuel cell electrolyte.

FIG. 5 illustrates a testing apparatus 50 for detecting cracks in a fuel cell electrolyte. In one embodiment, a plurality of electrolytes 5 can be provided on a support structure 51. In some embodiments, the support structure can be a partially or fully assembled fuel cell stack containing interconnects. Each of the electrolytes includes one or more conductive paths, as discussed above, and one or more contact areas 19 for connecting a probe across the respective paths. In one implementation, the probe 21 comprises an automated, robotic testing system that includes a contact element 53 that is moved into engagement with each contact area 19 on a carriage 55 and motion control system 57. The probe 21 measures a value associated with the current path and based on this value, determines whether the electrolyte contains a crack. A cracked electrolyte can then be removed from the fabrication process or from an assembled fuel cell stack. Alternatively, or in addition, as shown in FIG. 5, the probe 21 can include one or more lead wires 59 connected to the contact areas 19 for measuring the value associated with the current path. In certain embodiments, the lead wires 59 can remain connected after the stack is fully assembled and operational, so that the electrolytes can be monitored for cracks during operation of the system.

The embodiment methods and systems can be used to detect the presence of cracks over a wide range of temperatures (e.g., from below room temperature to 200° C. above stack operating temperature or more). The present technique can be used to detect cracks in an operating fuel cell application (e.g., when the stack is enclosed in a hot box and lead wires 59 are used to connect traces 17 to probe 21 located outside the hot box), as well as in a stand-alone test station, as shown in FIG. 5.

While ceramic electrolytes for a solid oxide fuel cell were described above as the tested objects, any other electrolytes, or any other ceramic material objects not associated with fuel cell systems may also be tested using the above methods and systems.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A method for testing an electrolyte material, comprising:
   providing an electrolyte material and a conductive path directly contacting the electrolyte material, the conductive path comprising at least one of a conductive trace and a wire;
   electrically connecting a probe across the conductive path; and
   measuring a value associated with the conductive path to determine the presence or absence of a crack in the electrolyte material,
   wherein the electrolyte material comprises an electrolyte for a solid oxide fuel cell; and
   wherein the conductive path is located on a cathode-side surface of the electrolyte material and at least partially surrounds a fuel riser opening extending though the electrolyte material.

2. The method of claim 1, wherein the value comprises a resistance of the path.

3. The method of claim 1, wherein the value comprises a current in the path.

4. The method of claim 1, further comprising:
   comparing the value with an expected or baseline value; and
   determining the presence of a crack based on a difference between the measured value and the expected or baseline value.

5. The method of claim 1, wherein providing the conductive path comprises providing the conductive trace on the electrolyte material using a thin-film or thick-film processing technique.

6. The method of claim 1, wherein:
   the conductive path has a width of between about 5 and 10 microns; and
   the conductive path has a height or thickness that is less than about 1 micron.

7. The method of claim 1, wherein providing the conductive path comprises providing the wire.

8. The method of claim 1, further comprising: at least one contact area on the electrolyte material for connecting a probe across the conductive trace.

9. The method of claim 1, wherein the conductive path is provided proximate to an opening or hole in the electrolyte material.

10. The method of claim 1, wherein the conductive path is provided proximate to an edge or corner of the electrolyte material.

11. The method of claim 1, further comprising providing a plurality of conductive paths on the electrolyte material.

12. The method of claim 1, wherein the electrolyte material comprises a ceramic material.

13. The method of claim 1, wherein the step of measuring the value is conducted at an operating temperature of the solid oxide fuel cell stack.

14. The method of claim 13, wherein the step of measuring the value is conducted while the electrolyte material is disposed in a fuel cell on a stack located in a hot box and while the stack is operating to generate electricity, the fuel cell stack comprising fuel cells and interconnects electrically connecting the fuel cells.

15. The method of claim 1, wherein the step of measuring the value is conducted at room temperature of a partially or fully assembled fuel cell stack in a test station before the stack is placed into a hot box.

16. The method of claim 1, wherein the conductive path comprises a noble metal trace.

17. The method of claim 1, wherein the conductive path comprises a conductive oxide trace.

18. The method of claim 1, wherein the probe comprises an ohmmeter.

19. A method for testing an electrolyte material, comprising:
   providing an electrolyte material and a conductive path comprising a conductive trace directly contacting the electrolyte material;
   electrically connecting a probe across the conductive path;
   providing a current to the conductive path to burn out the conductive path; and
   measuring a burnout characteristic of the conductive path to determine the presence or absence of a crack in the electrolyte material,
   wherein the electrolyte material comprises an electrolyte for a solid oxide fuel cell; and
   wherein the conductive path is located on a cathode-side surface of the electrolyte material and at least partially surrounds a fuel riser opening extending though the electrolyte material.

20. An apparatus for testing an electrolyte material, comprising:
   a support for holding an electrolyte material having a conductive path comprising at least one of a conductive trace and a wire directly contacting the electrolyte material;

a probe for making an electrical connection across the conductive path; and a measurement device coupled to the probe that measures an electrical characteristic of the conductive path to detect the presence or absence of a crack in the electrolyte material, wherein the electrolyte material comprises an electrolyte for a solid oxide fuel cell; and wherein the conductive path is located on a cathode-side surface of the electrolyte material and at least partially surrounds a fuel riser opening extending though the electrolyte material.

* * * * *